US008983160B2

(12) United States Patent
Chono

(10) Patent No.: US 8,983,160 B2
(45) Date of Patent: Mar. 17, 2015

(54) MEDICAL IMAGE DIAGNOSTIC APPARATUS AND VOLUME CALCULATING METHOD

(75) Inventor: Tomoaki Chono, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 609 days.

(21) Appl. No.: 13/259,366

(22) PCT Filed: Mar. 31, 2010

(86) PCT No.: PCT/JP2010/055798
§ 371 (c)(1),
(2), (4) Date: Sep. 23, 2011

(87) PCT Pub. No.: WO2010/113998
PCT Pub. Date: Oct. 7, 2010

(65) Prior Publication Data
US 2012/0027276 A1 Feb. 2, 2012

(30) Foreign Application Priority Data

Mar. 31, 2009 (JP) ................. 2009-086872

(51) Int. Cl.
G06K 9/00 (2006.01)
A61B 8/08 (2006.01)
(Continued)

(52) U.S. Cl.
CPC ............... A61B 8/08 (2013.01); A61B 5/02028 (2013.01); A61B 5/1075 (2013.01); A61B 8/065 (2013.01);
(Continued)

(58) Field of Classification Search
None
See application file for complete search history.

(56) References Cited

U.S. PATENT DOCUMENTS 8,419,641 B2 * 4/2013 Chono ........................ 600/437
2001/0025142 A1 * 9/2001 Wessels et al. ............. 600/425
(Continued)

FOREIGN PATENT DOCUMENTS

JP 2-200248 8/1990
JP 8-289877 11/1996
(Continued)

OTHER PUBLICATIONS

International Search Report and Written Opinion for PCT International Application No. PCT/JP2010/055798 Mailed Jun. 22, 2010.
(Continued)

Primary Examiner — Chan Park
Assistant Examiner — Mia M Thomas
(74) Attorney, Agent, or Firm — Brundidge & Stanger, P.C.

(57) ABSTRACT

A medical image diagnostic apparatus provided with an image acquisition unit configured to acquire in-vivo information about an object to be examined as a medical image, a display unit configured to display the medical image, a setting unit configured to set a target region of volume measurement in the medial image displayed on the display unit, a calculation unit configured to perform calculation to split the target region into a plurality of volume elements, calculate the moving distance of the vertices of the volume elements when the target region of the acquired medical image moves, calculate the volumes of the volume elements after the movement using the calculated moving distance of the vertices, totalizing the calculated volumes of the volume elements after the movement and using the total volume as the volume of the target region, and a control unit configured to display the volume of the target region on the display unit.

15 Claims, 10 Drawing Sheets

(51) Int. Cl.
*A61B 5/02* (2006.01)
*A61B 5/107* (2006.01)
*A61B 8/06* (2006.01)
*A61B 8/00* (2006.01)
*G06T 7/60* (2006.01)
*G06T 17/20* (2006.01)
*A61B 5/055* (2006.01)
*A61B 6/00* (2006.01)

(52) U.S. Cl.
CPC .............. *A61B 8/0883* (2013.01); *A61B 8/463* (2013.01); *A61B 8/466* (2013.01); *A61B 8/5223* (2013.01); *A61B 8/5238* (2013.01); *G06T 7/602* (2013.01); *G06T 17/20* (2013.01); *A61B 5/055* (2013.01); *A61B 6/503* (2013.01); *G06T 2207/30048* (2013.01)
USPC ................ 382/131; 600/437; 600/528; 378/4

(56) References Cited

U.S. PATENT DOCUMENTS

| | | | | |
|---|---|---|---|---|
| 2002/0147405 | A1* | 10/2002 | Denker et al. | 600/508 |
| 2003/0092998 | A1* | 5/2003 | Curiel | 600/481 |
| 2004/0044283 | A1* | 3/2004 | Yoneyama | 600/437 |
| 2004/0214882 | A1* | 10/2004 | Guthrie et al. | 514/456 |
| 2005/0111717 | A1* | 5/2005 | Yoshioka et al. | 382/128 |
| 2006/0171572 | A1* | 8/2006 | Breeuwer et al. | 382/128 |
| 2006/0239527 | A1* | 10/2006 | Krishnan et al. | 382/128 |
| 2007/0046661 | A1* | 3/2007 | Ma et al. | 345/419 |
| 2007/0167801 | A1* | 7/2007 | Webler et al. | 600/459 |
| 2008/0123927 | A1* | 5/2008 | Miga et al. | 382/131 |
| 2008/0146928 | A1* | 6/2008 | Dala-Krishna | 600/443 |
| 2008/0181479 | A1* | 7/2008 | Yang et al. | 382/131 |
| 2008/0262814 | A1* | 10/2008 | Zheng et al. | 703/11 |
| 2009/0010519 | A1* | 1/2009 | Wakai et al. | 382/131 |
| 2009/0238424 | A1* | 9/2009 | Arakita et al. | 382/128 |
| 2010/0087773 | A1* | 4/2010 | Ferrari | 604/7 |
| 2010/0215238 | A1* | 8/2010 | Lu et al. | 382/131 |
| 2011/0152684 | A1* | 6/2011 | Altmann et al. | 600/443 |
| 2011/0301454 | A1* | 12/2011 | Chono | 600/425 |
| 2012/0307961 | A1* | 12/2012 | Ikeda | 378/4 |
| 2013/0060156 | A1* | 3/2013 | Gregg et al. | 600/523 |
| 2014/0296714 | A1* | 10/2014 | Kuroki et al. | 600/450 |

FOREIGN PATENT DOCUMENTS

| | | |
|---|---|---|
| JP | 2004-121834 | 4/2004 |
| JP | 2006-247203 | 9/2006 |
| JP | 2007-014542 | 1/2007 |
| JP | 2007-507248 | 3/2007 |

OTHER PUBLICATIONS

Y. Watanabe, et al., "A Method to Estimate Volume and Surface Area of Organ by Two-Dimensional Echocardiography", IEEE Transactions on Biomedical Engineering, Mar. 1981, vol. BME-28, Issue 3, pp. 294-297.

J. Shanewise, MD et al., "ASE/SCA Guidelines For Performing a Comprehensive Intraoperative Multiplane Transesophageal Echocardiography Examination: Recommendations of the American Society of Echocardiography Council for Intraoperative Echocardiography and the Society of Cardiovascular Anesthesiologists Task Force for Certification in Perioperative Transeophageal Echocardiography", Journal of the American Society of Echocardiography, Oct. 1999, vol. 12, No. 10, pp. 884-900.

* cited by examiner

MEDICAL IMAGE DIAGNOSTIC APPARATUS AND VOLUME CALCULATING METHOD

FIELD OF THE INVENTION

The present invention relates to a medical image diagnostic apparatus and volume calculating method for measuring volume of an organ in a medical image of an organ including a motile organ such as a heart.

DESCRIPTION OF RELATED ART

Volume of a heart chamber which is one of the motile organs is calculated by a method referred to as the Simpson's method. The Simpson's method calculates volume of a cardiac chamber, for example in the case of using a medical image, by dividing a volumeter region of the cardiac chamber into a plurality of accumulated cylindrical disks and summing the respective disk volumes. The Simpson's method is disclosed, for example in Patent Document 1 and has been publicly known.

PRIOR PATENT DOCUMENTS

Patent Document 1: JP-T-2007-507248
Patent Document 2: JP-A-2006-247203

The inventor conducted verification on the following concrete case in the conventional Simpson's method.

That is, in the case of selecting the above-mentioned cylindrical disk in which a plurality of volumeter regions of the cardiac chamber are accumulated, in the phases of two heartbeats (a first phase and a second phase) from among the phases of different beats of a heart, distortion degrees of a first and a second disk were tentatively calculated between the phases of the first disk and the second disk having different split positions. As a result of the tentative calculations, distortion degrees of the first disk and the second disk had a great difference between the first phase and the second phase. Assuming that a disk represents a partial volume of a piece of a heart chamber accurately, the circumferential surface of the circular cylinder of the disk should always be touching the wall surface of the heart chamber. However in reality, since the disk has a cylindrical shape which approximates the partial volume of a piece of a heart chamber, degrees of distortion between the respective disks are different due to the heartbeats since the accumulated positions of the first disk and the second disk are different.

In other words, there is a problem in the conventional Simpson's method that the difference in distortion degrees of accumulation positions between the disks causes errors in volumeter calculation of the heart chamber.

The objective of the present invention is to provide a medial image diagnostic apparatus and volume calculation method capable of improving accuracy in volume calculation of an organ compared to the conventional Simpson's method.

BRIEF SUMMARY OF THE INVENTION

In order to achieve the above-described objective, the medical image diagnostic apparatus of the present invention comprises:
an image acquisition unit configured to acquire in-vivo information of an object to be examined as a medical image;
a display unit configured to display the medical image;
a setting unit configured to set a target region of volume measurement in the medical image displayed on the display unit;
a calculation unit configured to perform calculation for splitting the target region into a plurality of volume elements, calculate the moving distance of the vertices of the volume elements caused by moving of the target region in the obtained medical image, calculate volume of the volume elements after the movement using the calculated moving distance of the vertices, and set the summation of the calculated volumes of volume elements after the movement as the volume of the target region; and
a control unit configured to cause the display unit to display the volume of the target region.

In accordance with the above-described medical image diagnostic apparatus of the present invention, accuracy in volume calculation of an organ can be improved more than the conventional Simpson's method, since a polyhedron has a higher degree of conformity with respect to motion of an organ compared to a disk in the conventional Simpson's method and volume calculation is performed on a target region which is an organ using polyhedrons having higher degree of conformity.

In order to achieve the above-described objective, the volume calculation method of the present invention includes:
a first step of acquiring in-vivo information of an object as a medical image by an image acquisition unit;
a second step of displaying the medical image on a display unit;
a third step of setting a target region for volume measurement in the medical image displayed on the display unit by a setting unit;
a fourth step of performing calculation for splitting the target region into a plurality of volume elements by a calculation unit;
a fifth step of calculating moving distance of the vertices of the volume elements acquired by the calculation unit due to moving of the target region on the medical image;
a sixth step of calculating the volume of the volume elements after the movement using the moving distance of the vertices calculated by the calculation unit; and
a seventh step of summing the volumes of the volume elements after the movement calculated by the calculation unit and setting the result of summation as volume of the target region.

In accordance with the above-described volume calculation method of the present invention, accuracy in volume calculation of an organ can be improved more than the conventional Simpson's method, since a polyhedron has a higher degree of conformity with respect to motion of an organ compared to a disk in the conventional Simpson's method and volume calculation is performed on a target region which is an organ using the polyhedron having a higher degree of conformity.

EFFECT OF THE INVENTION

The present invention can provide the medical image diagnostic apparatus and volume calculation method capable of improving accuracy of volume calculation of an organ compared to the conventional Simpson's method.

DETAILED DESCRIPTION OF THE INVENTION

An embodiment of the present invention will be described below. The medical image diagnostic apparatus of the present invention is, for example an ultrasonic diagnostic apparatus, X-ray CT apparatus and MRI apparatus. The case of an ultrasonic diagnostic apparatus will be exemplified in embodiments of the present invention from among the medical image diagnostic apparatuses. Also, the present invention is not limited to the medical image diagnostic apparatus, and can be applied to various categories such as a medical image processing device. The various categories will be described later.

Embodiment 1

The first embodiment will be described in detail using FIG. 1~FIG. 4.

Figure 1:
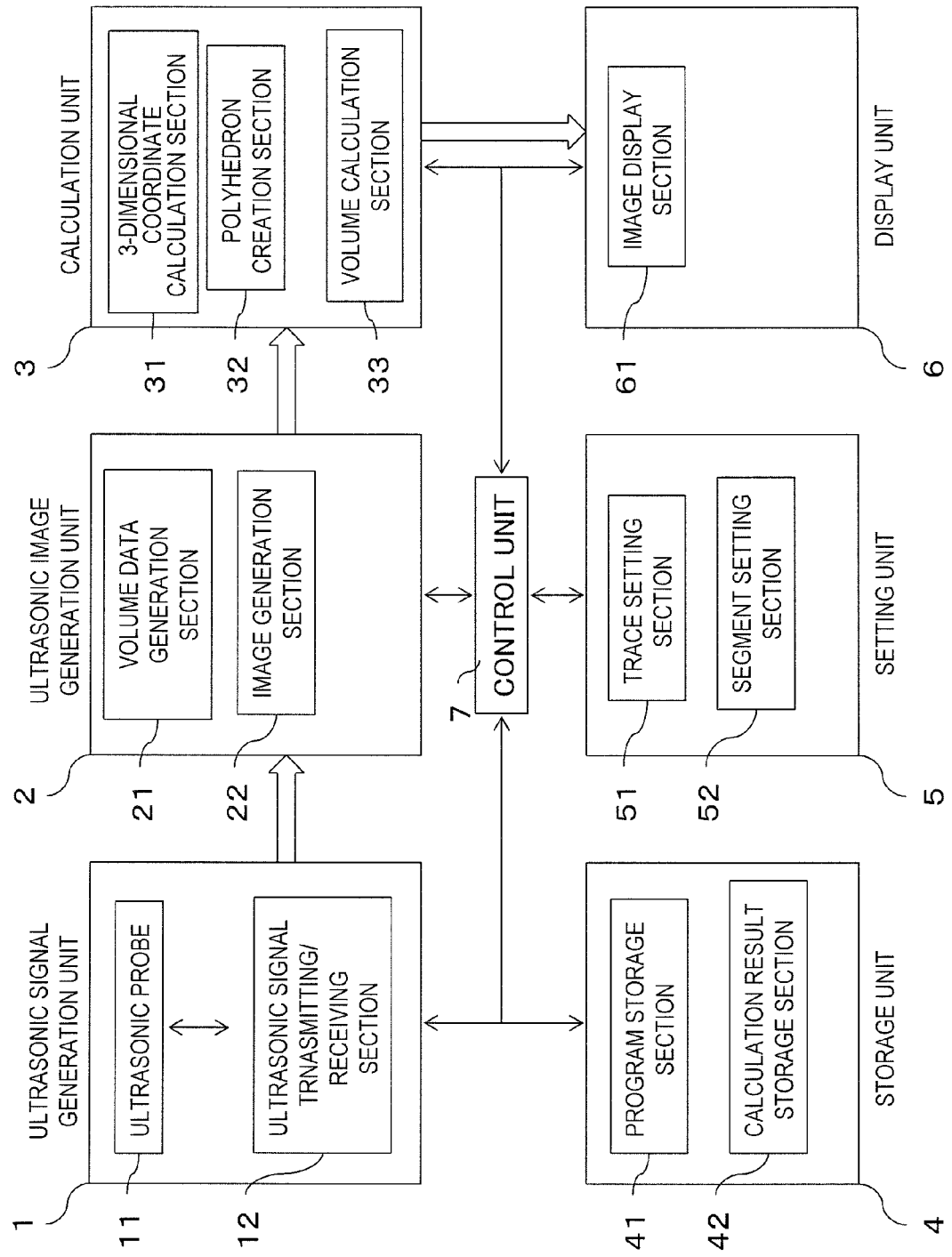
FIG. 1 is an example of a system configuration diagram of the ultrasonic image diagnostic apparatus in a first embodiment of the present invention.

FIG. 1 is an example of a system configuration diagram of the ultrasonic image diagnostic apparatus.

The ultrasonic diagnostic signal generation unit 1 comprises an ultrasonic probe 11 and an ultrasonic signal transmission/reception section 12, for transmitting an ultrasonic signal to the object and acquiring the reflected echo signal from the object.

The ultrasonic probe 11 comprises transducer elements having a scan method such as the linear type, convex type or sector type and capable of transmitting/receiving ultrasonic waves and arrayed in at least one-dimensional direction. The ultrasonic probe 11 is to be applied directly to an object so as to acquire ultrasonic signals of the object by transmission and reception of ultrasonic waves. An example of the ultrasonic probe 11 is a 2D-array probe in which the transducer elements capable of transmitting and receiving ultrasonic waves are 2-dimensionally arrayed, which can acquire 3-dimensional ultrasonic signals of the object by one time of ultrasonic-wave transmission and reception.

The same function as the 2D-array probe can also be achieved by a 1D-array probe. The 1D-array probe has transducer elements capable of transmitting/receiving ultrasonic waves that are arrayed therein one-dimensionally. The 1D-array probe can be operated almost in the same manner as 2D-array probe by the following operation. The operation is performed by moving the probe in the direction orthogonal to the array direction of the transducers while being applied to the object. The 1D-array probe can be moved manually by an operator or mechanically. The mechanical movement of the 1D-array probe can be executed, for example by oscillating the ultrasonic probe that scans a 2-dimensional cross-sectional surface by an ultrasonic signal in the direction orthogonal to the 2-dimensional cross-sectional surface so as to acquire a 3-dimensional ultrasonic signal as disclosed in Patent Document 2. The case of acquiring a 3-dimensional ultrasonic signal of the object using a 1D-array probe is included in the present embodiment.

The ultrasonic transmission/reception section 12 drives ultrasonic probe 11, transmits an ultrasonic signal to the object, receives the reflected echo signal from the object and performs signal processing such as amplification or phasing on the received reflected echo signal.

The ultrasonic image generation unit 2 comprises a volume data generation section 21 and image generation section 22, and has the function that generates 3-dimensional or 2-dimensional image from a 3-dimensional ultrasonic signals. The volume data generation section 21 generates a 3-dimensional image formed by voxel data from the 2-dimensional ultrasonic image inputted from ultrasonic signal generation unit 1. The volume data generation section 21 outputs the 3-dimensional image as it is when the image generated by the ultrasonic signal generation unit 1 is a 3-dimensional image. The image generation section 22 generates a 2-dimensional image from the 3-dimensional image.

The calculation unit 3 comprises a 3-dimensional coordinate calculation section 31, polyhedron generation section 32 and volume calculation section 33, and has the function that calculates 3-dimensional coordinates or volume. The 3-dimensional coordinate calculation section 31 calculates a trajectory of movement of the pixel that exists in the pre-set target region of which the 3-dimensional coordinates are calculated. The calculation for trajectory of the pixel is also referred to as the tracking operation.

The polyhedron generation unit 32 performs approximation operation of a polyhedron on the target region on which the 3-dimensional coordinate operation is performed. The approximation operation is performed by setting a plurality of vertices of a polyhedron on the border between the target region on which the 3-dimensional coordinate operation is performed and the region adjacent to the target region, and drawing line segments among the set plurality of vertices so as to form a polyhedron. The vertices of the polyhedron will be the object points to be used for a tracking operation.

The volume calculation section 33 calculates volume of the polyhedron generated by the polyhedron generation section 32, i.e. volume of the target region by the method to be described later.

The storage unit 4 comprises a program storage section 41 and a calculation result storage section 42, and has the function to store the algorithm calculated by calculation unit 3 or the programs for controlling the respective components by the control unit 7, or to store calculation results or ultrasonic signals. The storage unit 4 is a storage device such as a semiconductor memory, magnetic disk or optical disk.

The program storage section 41 stores the program containing algorithms such as the tracking operation, polyhedron generating operation and volume calculation for the calculation unit 3 to perform or the program for controlling the respective components.

The calculation result storage section 42 stores the calculation result data calculated by calculation unit 3, and the ultrasonic signal data, etc. outputted from the respective components. The measurement result data is used for the output to measurement reports.

The setting unit 5 comprises devices such as a keyboard, pointing device and switch to be operated by an examiner. In the present invention, it is the interface by which the examiner sets a target region.

Figure 3:
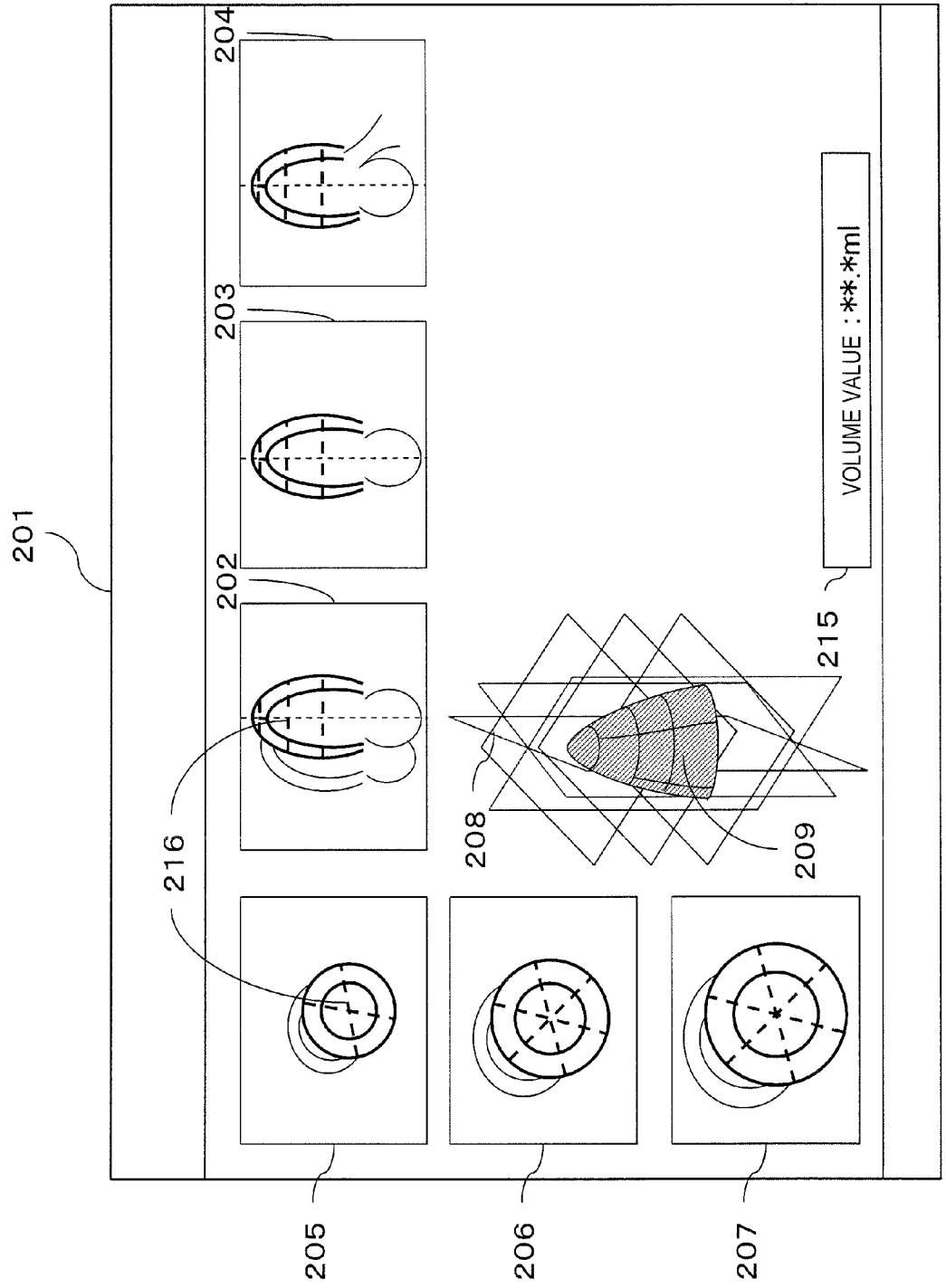
FIG. 3 is an example of a measurement screen in the ultrasonic image diagnostic apparatus of the first embodiment related to the present invention.

A trace setting section 51 is for the examiner to trace a depicted organ region in the ultrasonic image displayed on the display unit 6 using a pointing device. A heart is exemplified here as an organ. The trace setting section 51 executes the operation to trace the position of the endocardium and the epicardium of the region in which a heart is depicted on an image. Positional information of the endocardium and the epicardium is indicated by double thick lines as shown in a cross-section image 202 of FIG. 3. FIG. 3 is an example of a measurement screen of the ultrasonic image diagnostic apparatus in the first embodiment of the present invention. The outer thick line indicates the epicardium and the inner thick line indicates the endocardium. The positional information of the endocardium and the epicardium shows the position where the luminal region and the myocardial region are separated in the heart which is the target region of cardiac volume measurement. There are three operation methods here for the examiner to trace the region of the depicted organ.

(1) The method in which the examiner manually traces the entire positional information of the endocardium and the epicardium using a pointing device (manual operation). In concrete terms, positional information of the endocardium and the epicardium is inputted by the operator tracing the border of the regions equivalent to the endocardium and the epicardium while referring to the image of the heart region in the ultrasonic image displayed on the display unit 6. The control unit 7 causes the program storage section 41 to temporarily store the inputted positional information of the endocardium and the epicardium.

(2) The method in which the examiner inputs a plurality of points on the border of the endocardium region or the epicardium region using a pointing device and extracts the border of the endocardium or the epicardium by the inputted plurality of points on the border (semi-automatic operation). In concrete terms, the examiner inputs a plurality of border points between the region equivalent to the endocardium and the epicardium and the region adjacent to the equivalent region while referring to the image of the heart region in the ultrasonic image displayed on the display unit 6. The control unit 7 receives the inputted plurality of border points, connects them and causes the calculation unit 3 to execute the interpolation calculation such as the spline interpolation for acquiring the border line of the region as the positional information of the endocardium and the epicardium. The control unit 7 causes the program storage section 41 to temporarily store the inputted positional information of the endocardium and the epicardium.

(3) The method in which the examiner inputs the pixel points in the endocardium or the epicardium using a pointing device and extracts the border of the endocardial or epicardial region by the inputted pixel points (automatic operation). In concrete terms, the examiner inputs a point for specifying the region equivalent to the endocardium and the epicardium while referring to the image of the heart region in the ultrasonic image displayed on the display unit 6. The inputted point is used as the seed for the region growing method. The control unit 7 causes calculation unit 3 to execute the region extracting operation by the region growing method based on the seed so as to acquire the border line of the region as the positional information of the endocardium and the epicardium. The control unit 7 causes the program storage section 41 to temporarily store the acquired positional information of the endocardium and the epicardium.

A segment setting section 52 sets the border for splitting the heart region into a plurality of polyhedrons by a predetermined index with respect to every local domain.

An example of the index for a predetermined segmentation is the 16-splitting method or the 17-splitting method of myocardium which is recommended by ASE (American Society of Echocardiagraphy). The 17-splitting method, etc. is becoming the industry-wide standard in cardiac measurement to be executed by a medical image diagnostic apparatus. The examiner executes the 17-splitting method, etc. on myocardium by directly setting and inputting the 17-splitting positions on the myocardium on an image while referring to the image on the image display unit 61.

An LCD monitor, organic EL monitor or CRT can be used for the image display section 61 of the display unit 6, and the image display section 61 displays the 3-dimensional ultrasonic image or the 2-dimensional ultrasonic image outputted from the ultrasonic image generation unit 2 on a display screen.

The control unit 7 is respectively connected with the ultrasonic signal generation unit 1, the ultrasonic image generation unit 2, the calculation unit 3, the storage unit 4, the setting unit 5 and the display unit 6 so as to execute overall control of a series of process so that each process to be executed by the ultrasonic diagnostic apparatus from image measurement and volume calculation of an organ to image display can function properly. In other words, the control unit 7 functions as the central processing unit (CPU) in the computer system.

The above-described components function as below in the first embodiment. First in the first embodiment, the ultrasonic signal generation unit 1 acquires in-vivo information of an object as a medical image. The display unit 6 displays the acquired medical image. The setting unit 5 sets the target region for volume measurement in the medical image displayed on a display unit. The calculation unit 3 executes the calculation for splitting the target region into a plurality of volume elements, calculates the moving distance of the vertices of the volume elements caused by motion of the target region in the image, calculates the volume of the volume elements after the movement using the calculated moving distance of the vertices and the coordinates, sums up the calculated volumes of the volume elements and sets the summed up volume as the volume of the target region. The control unit 7 causes the display unit to display the volume of the target region.

Figure 2:
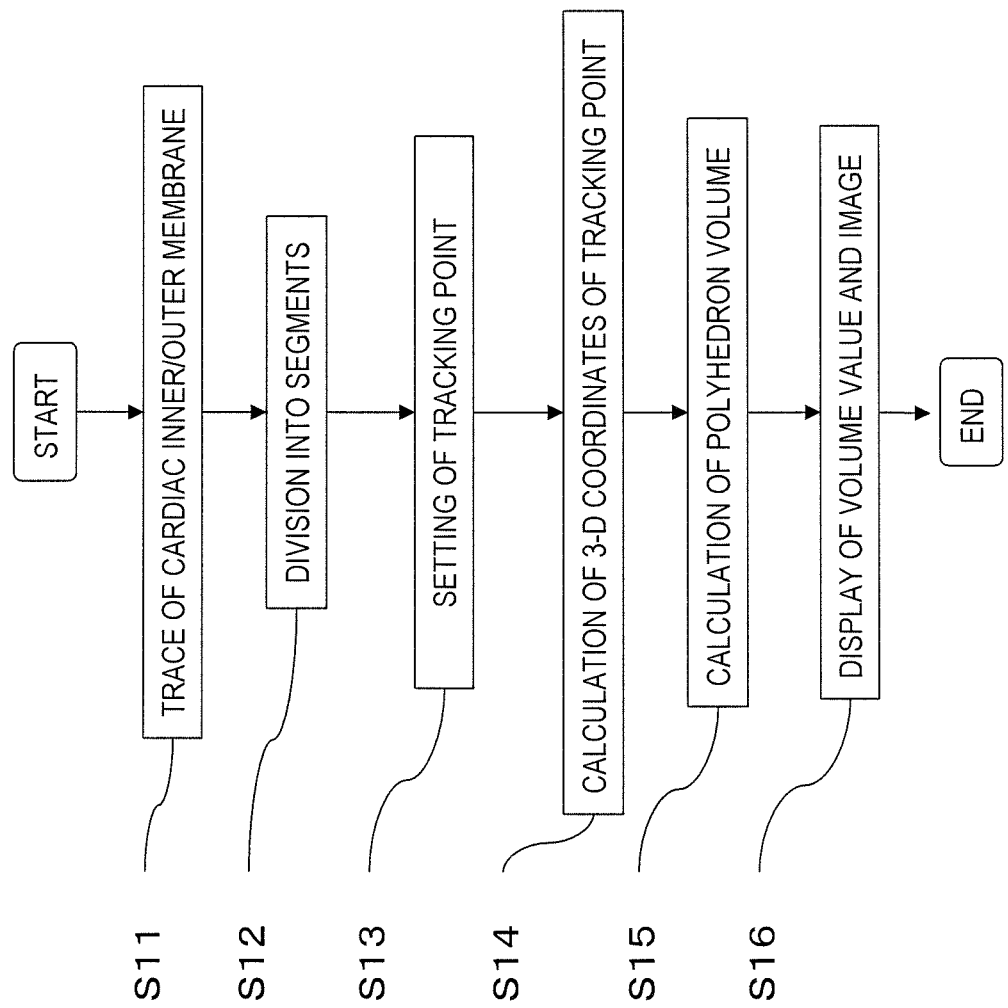
FIG. 2 is a flowchart of measurement process by the ultrasonic image diagnostic apparatus in the first embodiment of the present invention.

Next, an example of measurement process to be carried out by an ultrasonic diagnostic apparatus will be described using the flowchart shown in FIG. 2. FIG. 2 is the flowchart of measurement process to be executed by the ultrasonic diagnostic apparatus in the first embodiment of the present invention.

(Step S11)

The examiner generates a 3-dimensional ultrasonic image of an object in advance by applying the ultrasonic probe 11 of the ultrasonic signal generation unit 1 to the object and scanning a 2-dimensional ultrasonic image or a 3-dimensional ultrasonic image of the object's heart. The control unit 7 further reads in the 3-dimensional ultrasonic image generated by the volume data generation unit 21 from the ultrasonic signals generated by the ultrasonic signal generation unit 1 to the calculation result storage section 42, and causes the image display section 61 to display a 3-dimensional ultrasonic image 208 of the object's heart. The examiner sets positional information of the endocardium and the epicardium in the image of the object's heart shown as the thick lines in a cross-sectional image 202, etc. of FIG. 3 by the manual, semi-automatic or automatic operation to execute the above-described tracing using a pointing device provided in the setting unit 5. The control unit 7 receives the calculation result in the border of the region equivalent to the endocardium and the epicardium set by the examiner, and causes the program storage section 41 to temporarily store the positional information of the endocardium and the epicardium.

(Step S12)

The examiner sets the splitting positions of the myocardium in the endocardium or the epicardium to the segment setting section 52. The control unit 7 receives the setting of the segment setting section 52 and sets the splitting positions of the myocardium in the endocardium or the epicardium by manual operation of the examiner or calculation performed by the 3-dimensional coordinate calculation section 31.

In order to describe the concrete setting procedure, the method for manually setting a 3-dimensional ultrasonic image on the cross-sectional images 202~207 wherein the Multi Planar Reconstruction (MPR) process is executed and cut out as the 2-dimensional ultrasonic images will be described here. The cross-sectional images 202~207 are a cardiac apex four-chamber image 202, cardiac apex two-chamber image 203, cardiac apex long-axis image 204, short-axis cardiac apex image 205, short-axis papillary muscle image 206 and short-axis cardiac base image 207 to be the standard 2-dimensional cross-sectional images.

Also, the myocardium is divided into 16 segments based on the myocardial 16 splitting method which is recommended by the ASE. The breakdown of the 16 segments are: 6 segments of the short-axis cardiac base image 207, 6 segments of the short-axis papillary muscle image 206 and 4 segments of the short-axis cardiac apex image 206. The splitting positions of the segments are clearly specified by, for example a parting line 216 (thick dashed line). The examiner moves the position of the parting line using a pointing device in the setting unit 5 and sets the line to the splitting positions in the myocardium.

The examiner sets the splitting position in the circumferential direction on the short-axis cardiac apex image 205, short-axis papillary muscle image 206 and the short-axis cardiac base image 207, and also sets the splitting position in the long-axis direction on the cardiac apex images 202~204. The control unit 7 further receives the set cardiac splitting positions and causes the program storage section 41 to temporarily store the cardiac splitting positions.

(Step S13)

The control unit 7 reads out the endocardium and the epicardium set in step S11 and the splitting positions in the myocardium set in step S12 from the program storage section 41, and displays them by respectively superimposing them over apart of the cardiac apex four-chamber image 202, cardiac apex two-chamber image 203, cardiac apex long-axis image 204, short-axis cardiac apex image 205, short-axis papillary muscle image 206, short-axis cardiac base image 207 and 3-dimensional ultrasonic image 208 displayed on the display unit 6.

The examiner sets the position of the tracking point which moves due to heartbeats while referring to the endocardium and the epicardium set in step S11, the splitting position set in the myocardium in step S12 and the position of the respective images such as the cardiac apex four-chamber image 202 using the pointing device of the setting unit 5. The tracking point is set on the surface of the endocardium and the epicardium as well as on the side of the parting line 216 which indicates the border of the segment. The control unit 7 further receives the position of the set tracking point and causes the program storage section 41 to temporarily store the position of the tracking point.

(Step S14)

The control unit 7 reads out the position of the tracking point from the program storage section 41, and follows the same region in the image acquired at different times during heartbeats. The region having the highest degree of correlation is also included in the same region. As for the tracking method, for example the block matching method is used. The block matching method is a commonly-known method that cuts out a part of a first region including the tracking point of the processing target before the movement and a second region including the tracking point of the processing target after the movement, and searches the second region having the most approximated size, shape or pixel distribution to the first region.

Since the 3-dimensional coordinates of the first region before the movement are given when the MPR process is executed in step S12, the 3-dimensional coordinates of the second region after the movement can be acquired if the moving distance of the first region is obtained by the control unit 7 by breaking down the obtained relative distance in the axis direction of the reference axis of the 3-dimensional coordinates and adding the relative distance in the axis direction of the broken down reference axis and the 3-dimensional coordinates of the first region. Also, not the tracking point itself but the amplitude value of the RF signal in the vicinity of the tracking point or the image voxel value may also be used for the block matching method. Since the tracking operation can be obtained by the coordinates of the moved position in each volume of the respective tracking points, modification of the segment shape is also measured substantively at this time.

The control unit 7 further receives the acquired 3-dimensional coordinates of the second region, and causes the program storage section 41 to temporarily store the 3-dimensional coordinates of the second region.

(Step S15)

The control unit 7 reads out the tracking point and 3-dimensional coordinates of the second region from the program storage section 41, creates a plurality of volume elements (tetrahedrons here) having the tracking point as their vertex, and obtains volume of the segment from the summation of the created tetrahedrons. While a tetrahedron is exemplified in this step, the point is that a desired organ (measurement target) for measuring its volume is to be divided into a plurality of volume elements. The volume elements are disclosed in, for example "The basics of deformation and flux" by Takahiko Tanahashi, published by Sankei-sha in 2004.

The control unit 7 further causes the calculation unit 3 to obtain volume of the organ region by summing the segments, since an organ region to be measured such as a cardiac chamber is divided into a plurality of segments.

Figure 4:
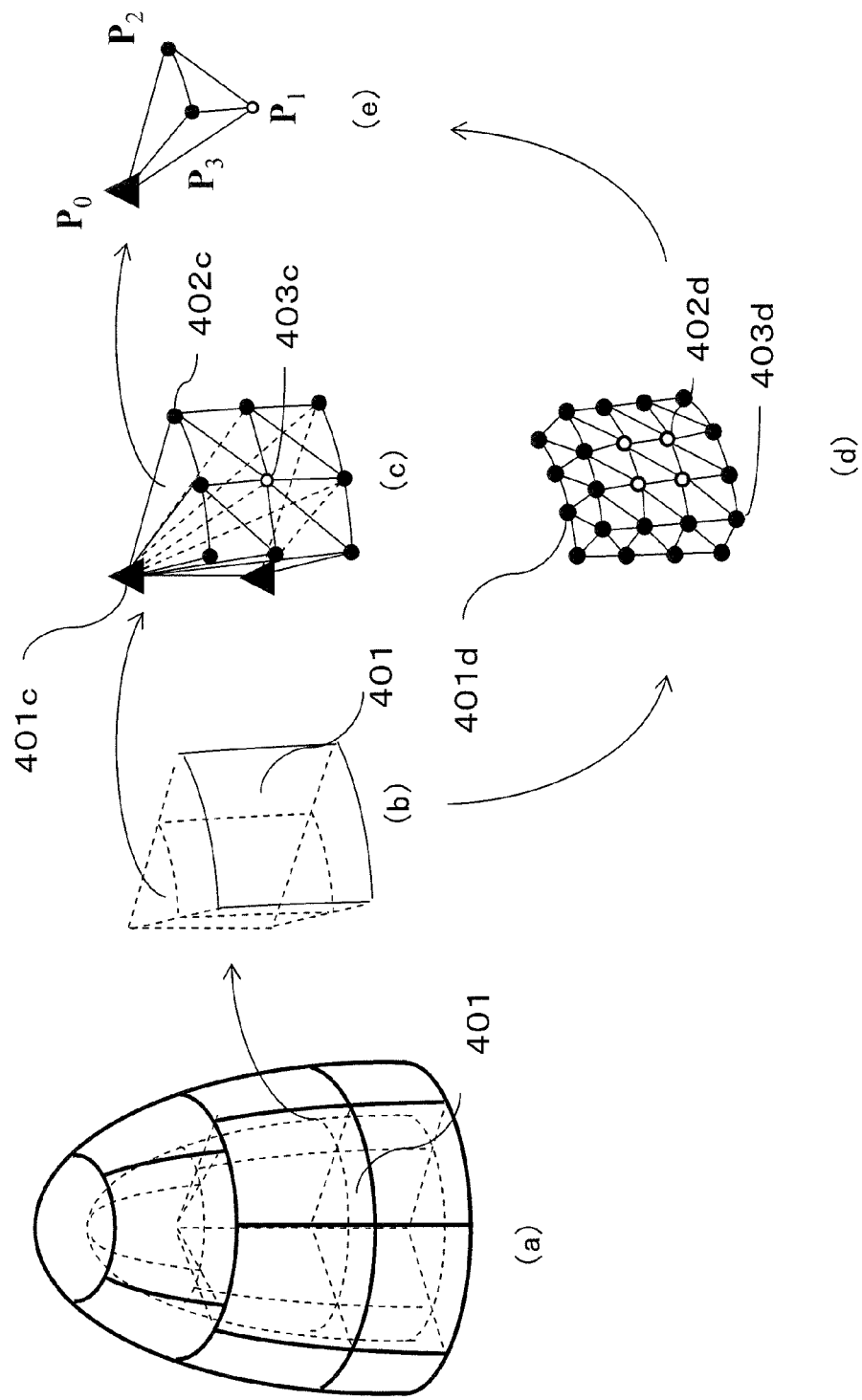
FIG. 4 shows the principle of segment division in step S12 of FIG. 2.

In concrete terms, the method for calculating the polyhedron volume for each segment is shown in FIG. 4. FIG. 4 is a diagram showing the principle of segment splitting described in step S12 of FIG. 2. FIG. 4(*a*) is an example of extracting a desired segment 401 from the entire left ventricle of a heart. FIG. 4(*b*) is an example of splitting the segment 501 into a cardiac chamber side segment 401*c* and a myocardium-side segment 401*d*. FIG. 4(*c*) is an example of placing the cardiac chamber side segment 401*c* by itself and further splitting the cardiac chamber side segment 401*c* into 10 tetrahedrons. In FIG. 4(*c*), a black circle 402*c* in the segment border is set as a tracking point and a tracking point 403*c* (white circle) is also set on the endocardium. FIG. 4(*d*) is an example of placing the myocardial side segment 401*d* by itself and further splitting the segment 401*d* into 18 tetrahedrons. In FIG. 4(*d*), a black circle 402*d* in the segment border is set as a tracking point and a tracking point 403*d* (white circle) is also set on the endocardium. In FIG. 4(e), one of the tetrahedrons which are broken down in FIG. 4(c) is presented.

The case that a segment is split into a plurality of (p-number of) tetrahedrons will be described below. The respective sides of one tetrahedron become a vector since they move due to heartbeats. When the sides of the tetrahedron are defined as vectors P0, P1, P2 and P3, volume vi of the tetrahedron can be expressed by the equation 1 which is one-sixth of the vectorial matrix based on P0.

$$vi = \frac{1}{6}\det(P_1 - P_0, P_2 - P_0, P_3 - P_0)$$ [Equation 1]

Also, volume Vsegment of the segment is the summation of volumes vi (i=1, 2, . . . , p) of the tetrahedron which can be expressed by the equation 2.

$$V_{segment} = \sum_{i=1}^{p} v(i)$$ [Equation 2]

Further, volume V of the entire organ can be expressed by the equation 2, assuming that the organ is split into q-number of segments, by summing volumes Vsegment (i=1, 2, . . . , q).

$$V = \sum_{j=1}^{q} V_{segment}(j)$$ [Equation 3]

The control unit 7 causes the calculation 3 to calculate volume of the cardiac chamber by summing only the segments on the cardiac chamber side. Also, the control unit 7 causes the calculation 3 to calculate volume of the cardiac muscle by summing only the segments on the cardiac muscle side. As for volume of a cardiac muscle, weight of the cardiac muscle can also be calculated by multiplying the calculated volume of the cardiac muscle by specific gravity of the cardiac muscle.

(Step S16)

The control unit 7 causes image display section 61 to display the cardiac apex four-chamber image 202, cardiac apex two-chamber image 203, cardiac apex long-axis image 204, short-axis cardiac apex image 205, short-axis papillary muscle image 206, short-axis cardiac base image 207 and 3-dimensional ultrasonic image 208, and also to display volume of an organ such as a cardiac chamber calculated by the measurement value display section 62 in step S15.

In accordance with the above-described first embodiment, it is possible to improve accuracy in volume calculation of an organ compared to the conventional Simpson's method, since polyhedrons have a higher degree of conformity with respect to motion of an organ compared to a disk of the conventional Simpson's method and volume calculation is performed on a target region which is an organ using polyhedrons having higher degree of conformity. Also, a characteristic effect of the first embodiment is that an examiner can perform calculation by setting the splitting process or the number of segment splits and polyhedrons as desires according to the degree of precision in volume calculation, in order to split a target organ for measuring its volume into segments or polyhedrons interactively. Also, both a cardiac chamber and a cardiac muscle of a heart can be measured in detail as a whole or for each segment. Also, since distortion of segments due to movement of the target organ is traced, volume change due to the distortion can be measured more accurately. Though the shape of a heart has complex irregularity, the volume can be easily calculated by performing polyhedron approximation.

Embodiment 2

Figure 5:
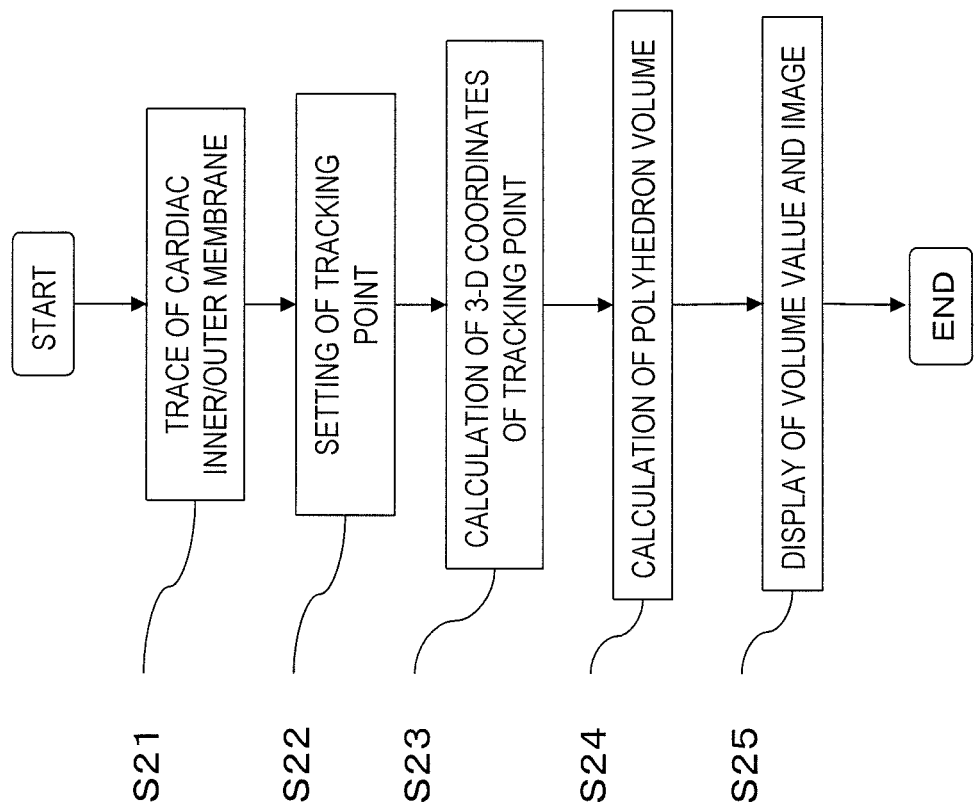
FIG. 5 is a flowchart of measurement process by the ultrasonic image diagnostic apparatus in a second embodiment of the present invention.

The second embodiment will be described in detail using FIG. 5 and FIG. 6.

The same ultrasonic diagnostic apparatus as the first embodiment will be exemplified below.

An example of measurement process by the ultrasonic diagnostic apparatus in the second embodiment related to the present invention will be described using the flowchart shown in FIG. 5. FIG. 5 is the flowchart showing measurement process by the ultrasonic diagnostic apparatus in the second embodiment related to the present invention.

(Step S21)

The examiner applies the ultrasonic probe 11 of the ultrasonic signal generation unit 1 to an object, and generates ultrasonic signals by scanning a 2-dimensional image or 3-dimensional image of the object's heart. The control unit 7 reads in the 3-dimensional ultrasonic image generated by the volume data generation section 21 to the calculation result storage section 42 from the ultrasonic signal generated by the ultrasonic signal generation unit 1, and causes the image display section 61 to display the 3-dimensional ultrasonic image 208 of the object' heart. The examiner sets positional information of the endocardium and the epicardium on the image of the object's heart by manual, semi-automatic or automatic operation for the above-described tracing process using a pointing device of the setting unit 5. The control unit 7 receives calculation of the border of the region equivalent to the endocardium and the epicardium set by the examiner, and causes the program storage section 41 to temporarily store the positional information of the endocardium and the epicardium.

(Step S22)

The control unit 7 reads out the endocardium and the epicardium set in step S21 from the program storage section 41, and displays them by respectively superimposing them over apart of the cardiac apex four-chamber image 202, cardiac apex two-chamber image 203, cardiac apex long-axis image 204, short-axis cardiac apex image 205, short-axis papillary muscle image 206, short-axis cardiac base image 207 and 3-dimensional ultrasonic image 208 displayed on the display unit 6.

The examiner sets the position of the tracking point which moves due to heartbeats while referring to the endocardium and the epicardium set in step S11, the split position of the heart muscle set in step S12 and the position of the respective images such as the cardiac apex four-chamber image 202 using the pointing device of the setting unit 5. The tracking point is set on the surface of the endocardium and the epicardium as well as on the side of the parting line 216 which indicates the border of segments. The control unit 7 further receives the position of the set tracking point and causes the program storage section 41 to temporarily store the position of the tracking point.

(Step S23)

Step S23 has the same process as step S14 in the first embodiment, thus the explanation thereof will be omitted.

(S24)

The control unit 7 reads out the tracking point and the 3-dimensional coordinates of the second region from the program storage section 41, creates a plurality of tetrahedrons having the tracking point at the vertex, and acquires volume of the segment by summing the created tetrahedrons. Further, volume of the organ region is acquired by summing the segments since the organ region such as a cardiac chamber which is the target for measurement is formed by a plurality of split segments.

Figure 6:
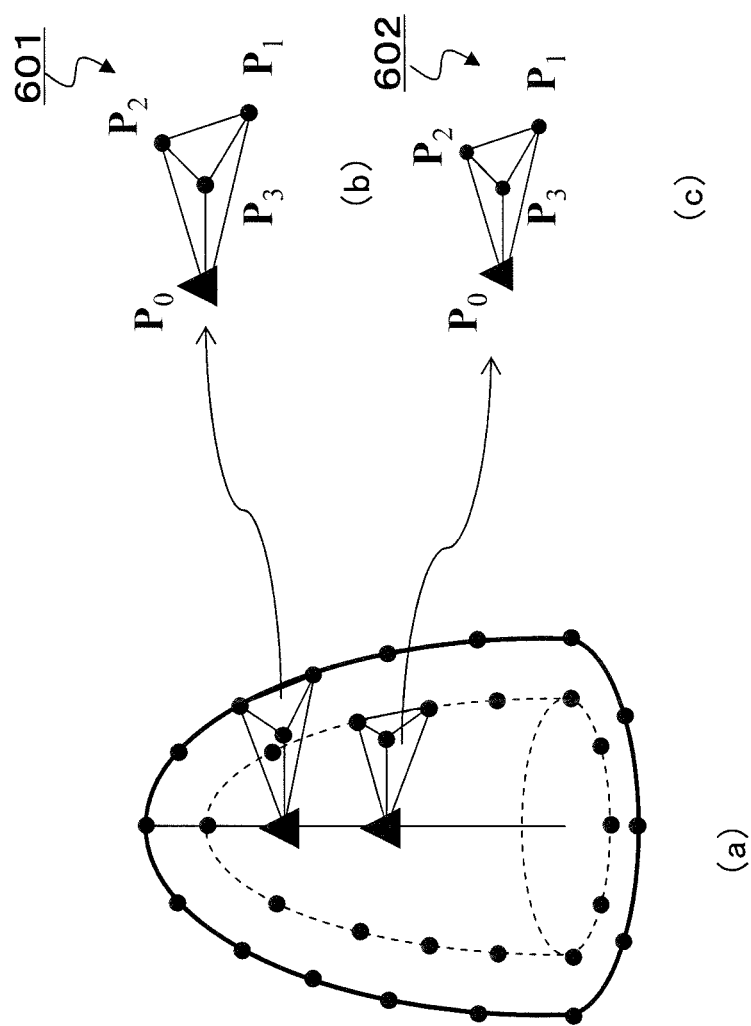
FIG. 6 shows the principle of volume calculation of polyhedrons in Step S24 of FIG. 5.

The concrete method for calculating volume of the polyhedrons for each segment is shown in FIG. 6. FIG. 6 is a principle diagram showing the volume calculation of polyhedrons illustrated in step S24 of FIG. 5. FIG. 6(*a*) shows an example of extracting a desired tetrahedron 601 on epicardium side and a tetrahedron 602 on the endocardium side from the whole left cardiac chamber of a heart. FIG. 6(*b*) shows an example of a target range for volume calculation of the tetrahedron 601 on the epicardium side. FIG. 6(*c*) shows an example of a target range for volume calculation of the tetrahedron 602 on the endocardium side.

Volume of one tetrahedron can be obtained by the matrix using four points of vectors as described in the first embodiment. By summing the volume of such obtained tetrahedron volumes in the whole region of the heart, the volume Vendo of the endocardium side and the volume Vepi on the epicardium side can be respectively obtained. The volume Vendo on the endocardium side is also the volume Vcavity of the cardiac chamber as it is. The volume Vmyocardium of the cardiac muscle can be obtained by subtracting volume Vendo on the endocardium side from the volume Vepi on the epicardium side.

(Step S25)

Step S25 has the same process as step S16 in the first embodiment, thus the explanation thereof will be omitted.

In accordance with the above-described second embodiment, since a polyhedron has a higher degree of conformity with respect to a target region of motion of an organ compared to a disk of the conventional Simpson's method and volume of the organ is calculated using the polyhedrons having higher degree of conformity, it is possible to improve accuracy in volume calculation of the organ compared to the conventional Simpson's method. Also, the characteristic effect of the second embodiment is that volume calculation of an organ can be performed by omitting the process for segment division described in the first embodiment.

Embodiment 3

The third embodiment explains an example for diagnosing a disease using information on volume of an organ acquired by the first embodiment or time change of the volume.

The third embodiment will be described in detail referring to FIG. 7~FIG. 10.

Figure 7:
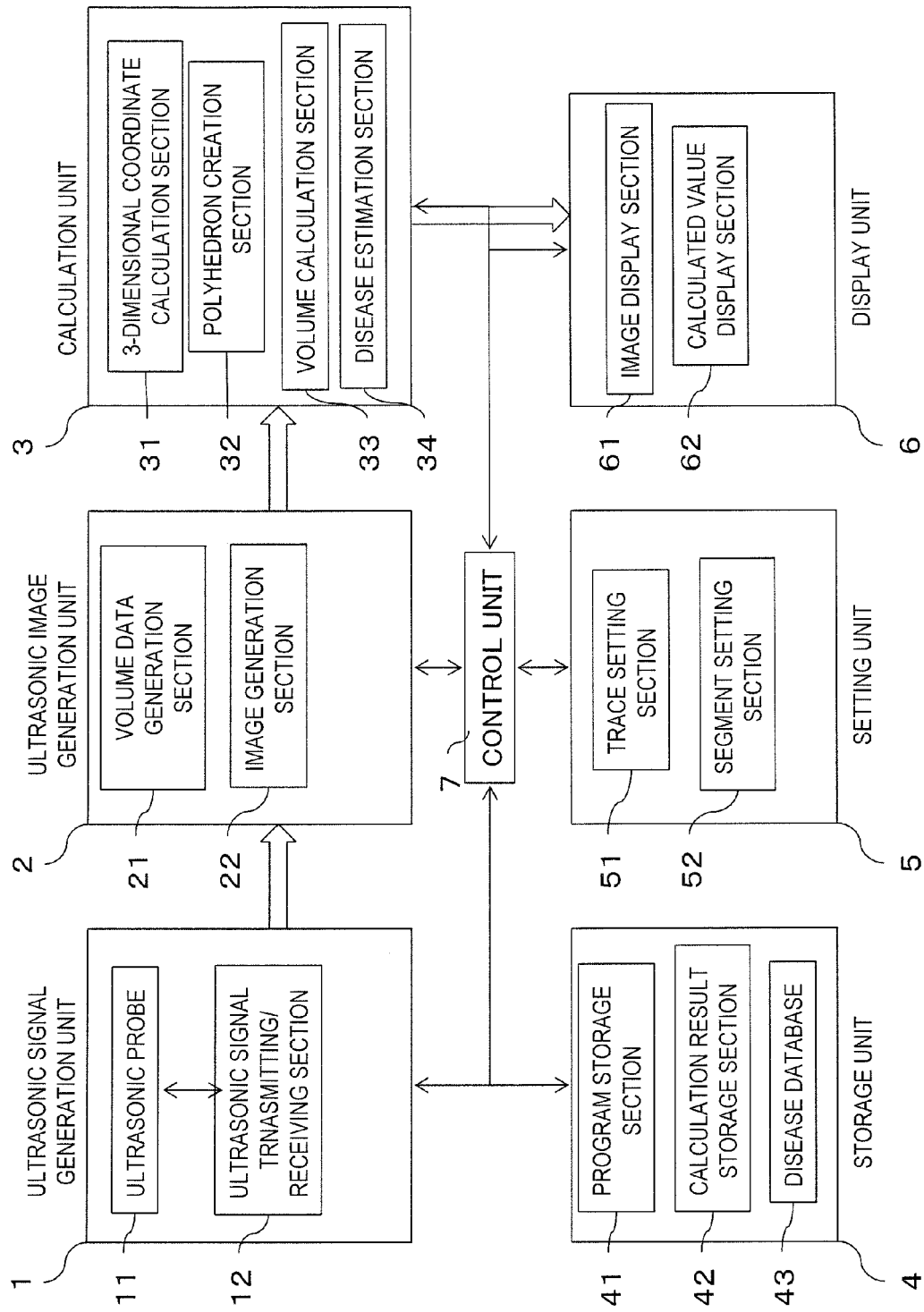
FIG. 7 is an example of the system configuration diagram in the ultrasonic image diagnostic apparatus of a third embodiment related to the present invention.

FIG. 7 is an example of a system configuration diagram of the ultrasonic diagnostic apparatus in the third embodiment related to the present invention.

In the system configuration diagram of the ultrasonic diagnostic apparatus in the third embodiment, description on the repeated components in the first embodiment will be omitted and only different components will be described.

To the calculation unit 3 in the third embodiment, a disease estimation section 34 is added to the 3-dimensional coordinate calculation section 31, the polyhedron creation section 32 and the volume calculation section 33.

The disease estimation section 34 estimates the kind of diseases from time change of the volume values of the left ventricle calculated by the volume calculation section 33.

In the storage unit 4, a disease database 43 will be added to the program storage section 41 and the calculation result storage section 42.

The disease database 43 is to be referred to by the disease estimation section 34, and typical images of the cases such as dilated cardiomyopathy, hypertrophic cardiomyopathy, local wall motion abnormality and myocardial asynchronous abnormal shrinkage from among the medical images are categorized and stored in accordance with the progression of disease.

Dilated cardiomyopathy will be described below as a concrete example.

Dilated cardiomyopathy occupies a majority of serious heart failure, and is suspected when inner cavity of a left ventricle of an object is enlarged in an image diagnosis.

Doctors confirm diagnosis of dilated cardiomyopathy when both enlargement of inner cavity volume of a left ventricle and weakening in cardiac contractive force are recognized. The index for confirming diagnosis of dilated cardiomyopathy is that enlargement is recognized in the diameter of the entire left ventricle and also in the inner cavity thereof, and that ejection fraction of the left ventricle is recognized as less than 50% in the result of echocardiogram and contrast study of the left ventricle. The left ventricle ejection fraction is the value that the ejection volume is divided by the volume of the heart when enlarged, which is used as the index to indicate the pumping ability of the heart. The ejection volume is the blood volume pumped out when the left ventricle is deflated one time which is the volume of the heart when deflated is subtracted from the volume when the heart is enlarged.

Figure 9:
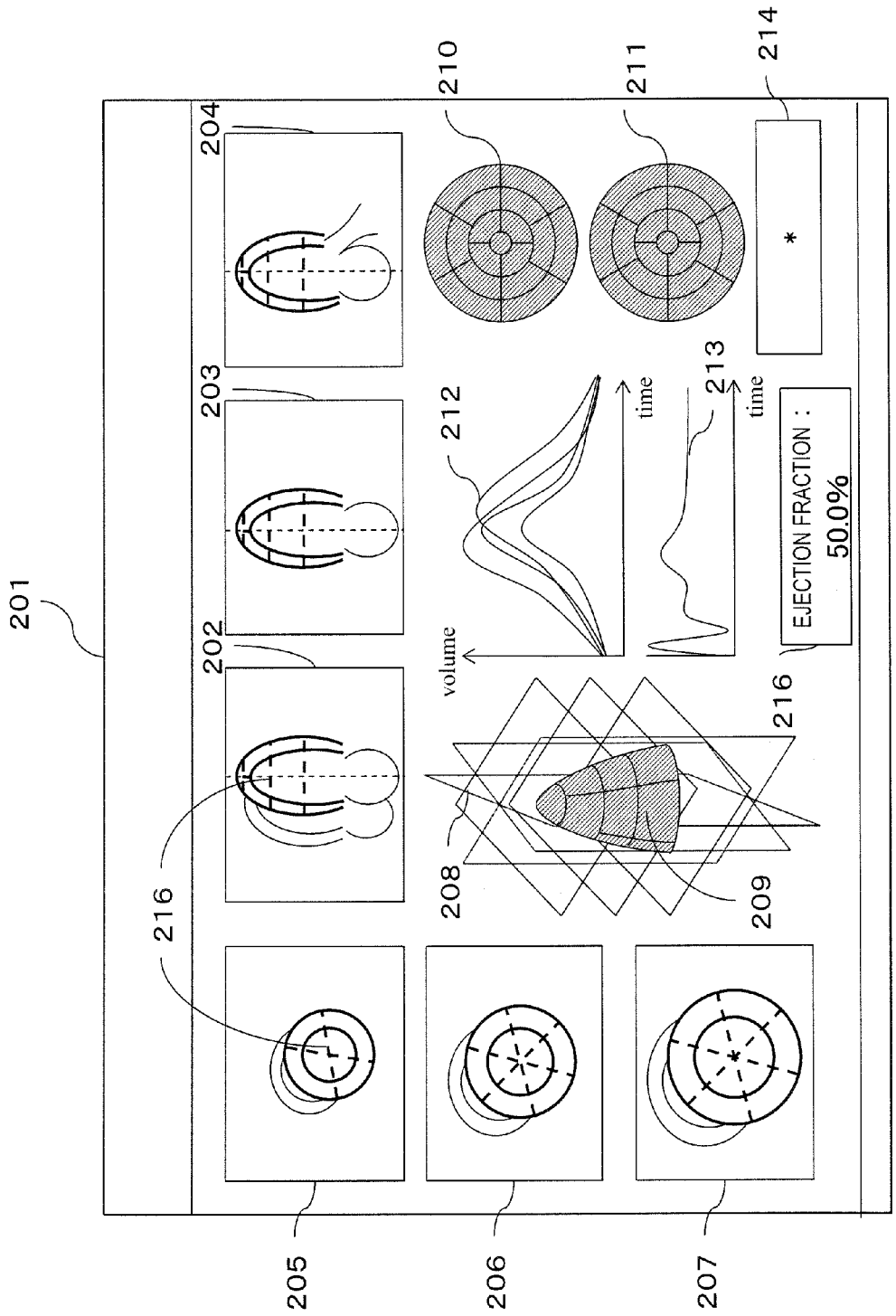
FIG. 9 is an example of a measurement screen in the ultrasonic image diagnostic apparatus of the third embodiment related to the present invention.

Given this factor, a reference image of the enlarged whole left ventricle and reference images having for example, 70%, 60%, 50%, 40% and 30% of left ventricle ejection fraction are stored in the disease database 43. Examples of the reference images are the cardiac apex four-chamber image 202, cardiac apex two-chamber image 203, cardiac apex long-axis image 204, short-axis cardiac apex image 205, short-axis papillary muscle image 206 and short-axis cardiac base image 207 shown in FIG. 9. FIG. 9 is an example of a measurement screen of the ultrasonic diagnostic apparatus in the third embodiment related to the present invention.

The disease estimation section 34 performs comparison operation on the reference image read out from the disease database 43 and, for example the cardiac apex two-chamber image from among the actually-measured images of the object. The comparison operation is performed by sequentially subtracting the actually measured cardiac apex two-chamber image from the images having 70%, 60%, 50% and 40% of left-ventricle ejection fraction from among the cardiac apex two-chamber images of the reference images. Then by defining the left-ventricle ejection fraction supposedly as 70% (normal), 60% (mild case), 50% (moderate case) and 40% (severe case), doctors can use it as the information for making diagnosis from the actually measured image by setting the case having the smallest difference between the reference image and the actually measured image as the extent of dilated cardiomyopathy. Also, in the case that the size of the reference image and the actually-measured image are different at the time of performing the comparison operation, the comparison operation can be carried out by extracting the respective contours of the reference image and the actually-measured image, obtaining the respective areas of the reference image and the actually-measured image in which the contours are extracted, and implementing the image enlargement (or reduction) process to match one image to the other image using the ratio of the obtained respective areas so that the same size images can be compared.

The calculation value display section 62 in the third embodiment displays the volume value of an organ such as the left ventricle of a heart calculated by the volume calculation section 33 on a display screen.

In a measurement screen of FIG. 9, the volume value or the rapidity of change is displayed on a 3-dimensional film surface on a display 209 by adding a hue. Means of adding a hue may be carried out for each segment, or for each tetrahedron which makes it possible to present more detailed variation.

Also, the volume value or the rapidity of change can be displayed by pseudo-colorizing on a bull's-eye pattern. These are displayed as a bull's eye 210 of a myocardial segment and a bull's eye 211 of a cardiac-chamber segment. The volume change in the entire organ or in the respective segments can be displayed graphically in a display 212. Any combination of values such as the total value or average value of segments in the cardiac apex image 205, the papillary muscle image 206 and the cardiac base image 207 can be displayed. These are displayed being synthesized with a biological signal 213 such as an electrocardiogram or phonocardiogram. Since volume change of the entire cardiac lumen can be calculated, the left ventricle ejection fraction can also be calculated and displayed as display 215. Further, the name of disease which is estimated by the disease estimation section 34 is displayed in display 214. These calculation results are stored in the calculation result storage section 42.

Figure 10:
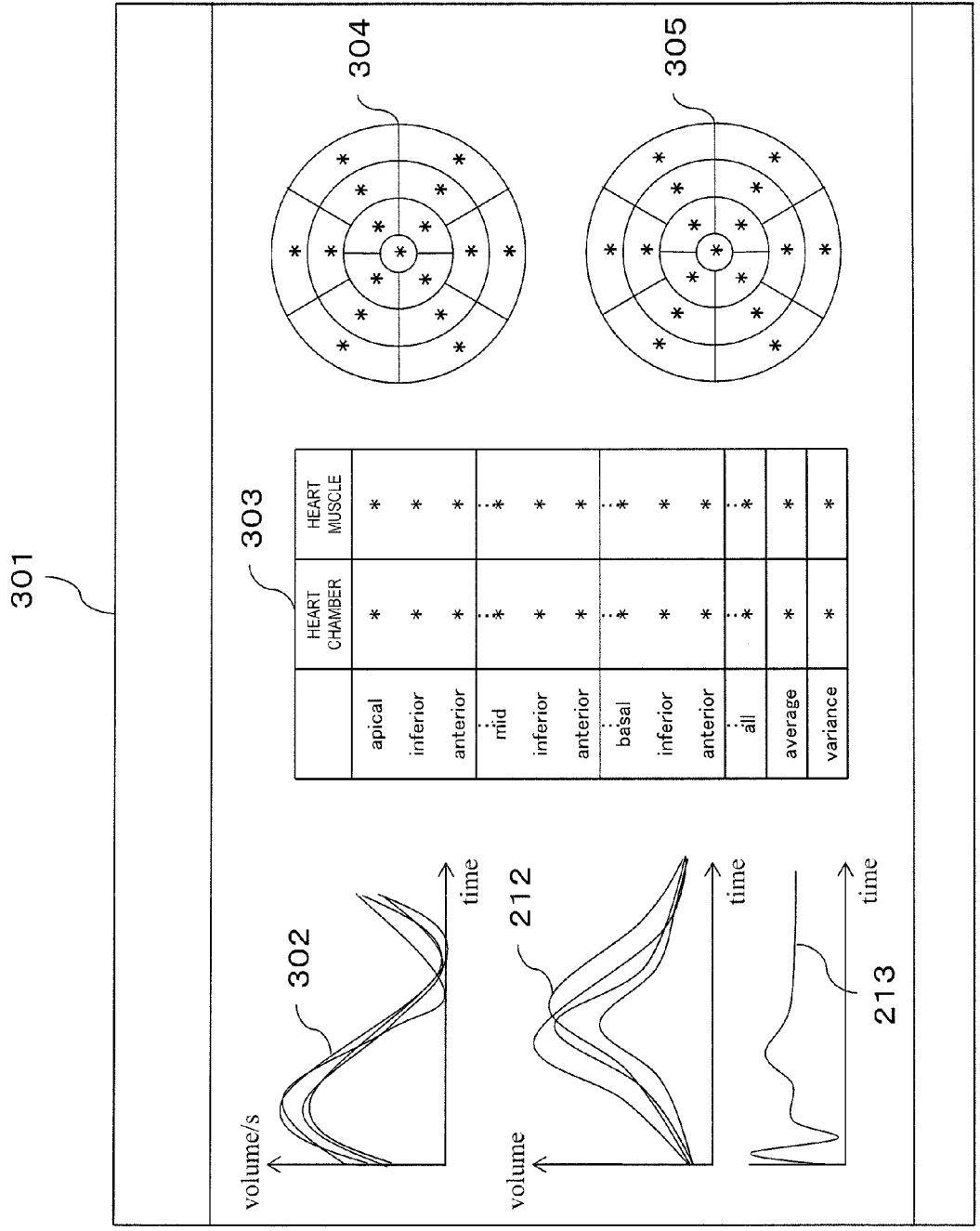
FIG. 10 is an example showing a modified pattern of the measurement screen in FIG. 9.

Also, ultrasonic diagnostic image or graphs may also be displayed using the display pattern shown in FIG. 10. FIG. 10 is an example for explaining another pattern of the measurement screen in FIG. 9. An image 301 is exemplified in FIG. 10. The biological signals and the measurement values which change with time such as volume curves or volume change velocity curves are displayed on the left side of FIG. 10. Various measurement values are displayed using a chart in the center of FIG. 10. For example, the maximum and minimum values or the time to reach the maximum and minimum values of the respective 17 segments are displayed. Also, the indexes in relation to the average or dispersion for each of the 17 segments are displayed. In the bull's-eye display on the right side of FIG. 10, the measurement values are numerically displayed in the respective segments (*-marks in the diagram).

Figure 8:
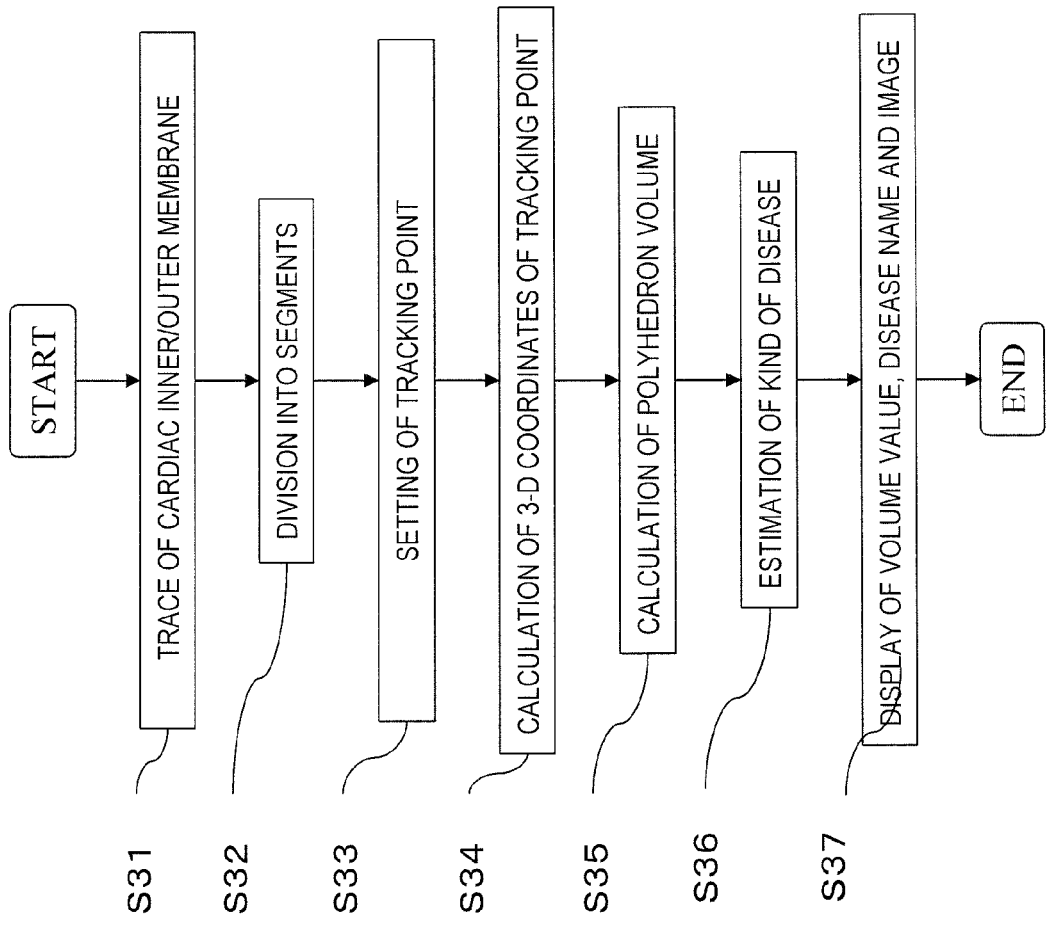
FIG. 8 is a flowchart of measurement process by the ultrasonic image diagnostic apparatus in the third embodiment related to the present invention.

Next, an example of measurement process by the ultrasonic diagnostic apparatus in the third embodiment of the present invention will be described using the flowchart shown in FIG. 8. FIG. 8 is a flowchart showing a measurement process by the ultrasonic diagnostic apparatus in the third embodiment of the present invention.

The explanation on step S31~step S35 will be omitted since they are the same as in the first embodiment.

(Step S36)

The control unit 7 causes the disease estimation section 34 to perform comparison operation on the reference image read out from the disease database 43 and the cardiac apex two-chamber image from among the actually-measured images of the object. In the comparison operation, the progression degree of the dilated cardiomyopathy in the actually-measured image is outputted based on the left ventricle ejection fraction of the cardiac apex two-chamber image from among the reference images. The example of this output here is a moderate case (left ventricle ejection fraction: 50%).

The control unit 7 further receives the left ventricle ejection fraction and the progression degree of dilated cardiomyopathy, and temporarily stores the messages regarding the value of left ventricle ejection fraction and the progression degree of the dilated cardiomyopathy. The message is, for example "possible mild case of dilated cardiomyopathy".

(Step S37)

The control unit 7 causes the image display section 61 to display the cardiac apex four-chamber image 202, cardiac apex two-chamber image 203, cardiac apex long-axis image 204, short-axis cardiac apex image 205, short-axis papillary muscle image 206, short-axis cardiac base image 207 and 3-dimensional ultrasonic image 208, and time change of the volume of an organ such as a ventricle calculated in step S15 by the measurement value display section 62 as a graph 212.

Also, the control unit 7 displays a left-ventricle ejection fraction 216 as "ejection fraction: 50%" and a message 214 saying "possible moderate case of dilated cardiomyopathy" on the image screen as the index for diagnosis by doctors.

In accordance with the above-described third embodiment, since a polyhedron has a higher degree of conformity with respect to motion of an organ for every time series compared to a disk of the conventional Simpson's method and volume of the organ is calculated using the polyhedrons having higher degree of conformity, it is possible to improve accuracy in volume calculation of the organ compared to the conventional Simpson's method.

Also, the characteristic effect of the third embodiment is to provide an aid to doctors for diagnosis by displaying the index of diseases determined from the displacement of volume of an organ using the time change of volume calculation of the organ.

Since the control unit 7 can calculate the timing for imaging inversely from the time change of the organ volume such as the maximum volume or the minimum volume and the actual imaging can be executed at the calculated timing, it is possible to execute scanning of ultrasonic images without being influenced by individual differences in movement velocity of the organ.

While a medical image diagnostic apparatus is exemplified in the respective embodiments, the invention can be applied to a medical image processing apparatus by replacing the image acquisition unit (ultrasonic signal generation unit) with an image input unit.

In this case, the ultrasonic signal generation unit is replaced with the image input unit, and has the following configuration.

The ultrasonic image processing apparatus comprises the ultrasonic image input unit, an ultrasonic image generation unit, a calculation unit, a storage unit, a setting unit, a display unit and a control unit.

The ultrasonic image input unit comprises at least one of an external storage media and network drive, and has function to input ultrasonic images.

The external storage media is a storage media such as a flexible disk (FD), magnetic disk, optical disk, optical magnetic disk, USB memory, ZIP memory and SSD memory in which ultrasonic images are stored, capable of reading the ultrasonic images from a computer system by being loaded in the ultrasonic image processing apparatus if it is a disk or being connected thereto if it is a memory.

The network drive in the local area network (LAN) enclosed in a facility such as a hospital is capable of reading the ultrasonic images from computer system via a server which is installed in the facility and connected to the LAN. Also, the network drive which is connected to a wide area network (WAN) in a wide communication line is capable of reading the ultrasonic images from computer system via an external server connected to the WAN.

INDUSTRIAL APPLICABILITY

The present invention can be applied to various medical image diagnostic apparatuses such as an X-ray CT apparatus and an MRI apparatus. Also, the present invention can be used for IT devices capable of processing images obtained from medical image diagnostic apparatuses, such as a computer and various mobile terminals.

DESCRIPTION OF REFERENCE NUMERALS

1: ultrasonic signal generation unit, 2: ultrasonic image generation unit, 3: calculation unit, 4: storage unit, 5: setting unit, 6; display unit, 7: control unit

The invention claimed is:

1. A medical image diagnostic apparatus comprising:
an image acquisition unit configured to acquire in-vivo information of an object to be examined as a medical image;
a display unit configured to display the medical image;
a setting unit configured to set a target region for volume measurement in the medical image displayed on the display unit;
a calculation unit configured to perform a calculation to split the target region into a plurality of volume elements, calculate a moving distance of the vertices of the plurality of volume elements caused by the movement of the target region in the acquired medical image, calculate a volume of the plurality of volume elements after the movement using the calculated moving distance of the vertices, sum the calculated volumes of the plurality of volume elements after the movement, and set the summed volumes as the volume of the target region; and
a control unit configured to cause the display unit to display the volume of the target region,
wherein the plurality of volume elements split by the calculation unit comprises a first volume element, which is disposed on the outer side of a cardiac chamber of a heart, and a second volume element, which is disposed on the inner side of the cardiac chamber of the heart,
wherein the image acquisition unit acquires in-vivo information of the object as a medical image in time series, and
wherein the calculation unit calculates the moving distance of the vertices of the plurality of volume elements in time series, calculates volume of the plurality of volume elements in time series based on the moving distance of the vertices, and sums the calculated volumes of the plurality of volume elements in time series.

2. The medical image diagnostic apparatus according to claim 1, wherein the calculation unit performs a calculation to split the target region into a plurality of polyhedrons, and to further split the plurality of polyhedrons into the plurality of volume elements.

3. The medical image diagnostic apparatus according to claim 2, wherein the calculation unit calculates a volume of each polyhedron of the plurality of polyhedrons by obtaining an individual volume of a plurality of tetrahedrons which form the polyhedron and summing the obtained volumes of individual volume elements of the plurality of volume elements.

4. The medical image diagnostic apparatus according to claim 2, wherein the calculation unit calculates a volume of the target region by obtaining the individual volume of the plurality of polyhedrons which form the target region and summing the obtained volumes of individual polyhedrons.

5. The medical image diagnostic apparatus according to claim 2, wherein the control unit causes the display unit to superimpose and display the parting lines by which the target region is split into the plurality of polyhedrons over a two-dimensional image or a three-dimensional image showing the target region.

6. The medical image diagnostic apparatus according to claim 2,
wherein the target region includes a heart, and
wherein the setting unit splits the target region into the plurality of polyhedrons in accordance with the method for splitting a cardiac muscle into a predetermined number of sections.

7. The medical image diagnostic apparatus according to claim 1, wherein the control unit causes the display unit to superimpose and display on the display unit the partition lines by which the target region is split into the volume elements with the two-dimensional image or the three-dimensional image showing the target region.

8. The medical image diagnostic apparatus according to claim 1,
wherein the target region includes a heart, and
wherein the control unit causes the calculation unit to calculate the left ventricle ejection fraction and the display unit to display the calculated left ventricle ejection fraction on the display unit.

9. The medical image diagnostic apparatus according to claim 1,
wherein the target region includes a heart, and
wherein the control unit causes the calculation unit to create a message to support diagnosis based on the left ventricle ejection fraction and the display unit to display the message for supporting diagnosis.

10. The medical image diagnostic apparatus according to claim 1, wherein the outer side is an epicardium side, and the inner side is an endocardium side.

11. The medical image diagnostic apparatus according to claim 1, wherein each of the first volume element and the second volume element is a tetrahedron.

12. The medical image diagnostic apparatus according to claim 11, wherein one vertex of the tetrahedron is disposed on the center line, which is located at the center of the target region.

13. A medical image diagnostic apparatus comprising:
a image acquisition unit configured to acquire in-vivo information of an object to be examined as a medical image;
a display unit configured to display the medical image;
a setting unit configured to set a target region for volume measurement in the medical image displayed on the display unit;
a calculation unit configured to perform a calculation to split the target region into a plurality of volume elements, calculate a moving distance of the vertices of the plurality of volume elements caused by the movement of the target region in the acquired medical image, calculate a volume of the plurality of volume elements after the movement using the calculated moving distance of the vertices, sum the calculated volumes of the plurality of volume elements after the movement, and set the summed volumes as the volume of the target region; and
a control unit configured to cause the display unit to display the volume of the target region,
wherein the plurality of volume elements split by the calculation unit comprises a first volume element, which is disposed on the outer side of a cardiac chamber of a heart, and a second volume element, which is disposed on the inner side of the cardiac chamber of the heart, wherein the calculation unit performs a calculation to split the target region into a plurality of polyhedrons, and to further split the plurality of polyhedrons into the plurality of volume elements, wherein the control unit causes the display unit to superimpose and display the parting lines by which the target region is split into the plurality of polyhedrons over a two-dimensional image or a three-dimensional image showing the target region, wherein the setting unit further comprises a function to set a tracking point in the case that the size or shape of the target region changes over time, and wherein the control unit causes the display unit to superimpose and display on the display unit the set tracking point with the parting lines.

14. The medical image diagnostic apparatus according to claim 13, wherein the control unit tracks the same region in the image acquired at different times including the set tracking point.

15. A volume calculation method including:
- a first step of acquiring in-vivo information of an object to be examined as a medical image by an image acquisition unit;
- a second step of displaying the medical image on a display unit;
- a third step of setting, by the setting unit, a target region for volume measurement in the medical image displayed on the display unit;
- a fourth step of performing, by the calculation unit, a calculation for splitting the target region into a plurality of volume elements;
- a fifth step of calculating a moving distance of the vertices of the plurality of volume elements caused by movement of the target region in the medical image acquired by the calculation unit;
- a sixth step of calculating volume of the plurality of volume elements after the movement using the moving distance of the vertices calculated by the calculation unit; and
- a seventh step of summing the volumes of the plurality of volume elements after the movement calculated by the calculation unit and setting the summed volumes as the volume of the target region, wherein the plurality of volume elements split by the calculation unit comprises a first volume element, which is disposed on the outer side of a cardiac chamber of a heart, and a second volume element, which is disposed on the inner side of the cardiac chamber of the heart, wherein the first step acquires in-vivo information of an object as a medical image in time series, wherein the fifth step calculates moving distance of the vertices of the volume elements in time series, wherein the sixth step calculates volume of the volume elements after the movement based on the moving distance of the vertices in time series, and wherein the seventh step sums the calculated volumes of volume elements after the movement in time series.

* * * * *